US012653486B2

(12) United States Patent
Chou et al.

(10) Patent No.: US 12,653,486 B2
(45) Date of Patent: Jun. 16, 2026

(54) EQUIPMENT FOR MONITORING PHYSIOLOGICAL STATUS

(71) Applicant: Taipei Medical University, Taipei City (TW)

(72) Inventors: Pai-Chien Chou, Taipei City (TW); Chien-Hua Chen, Taipei City (TW); Ya-Ting Juang, Taipei City (TW)

(73) Assignee: Taipei Medical University, Taipei City (TW)

( * ) Notice: Subject to any disclaimer, the term of this patent is extended or adjusted under 35 U.S.C. 154(b) by 362 days.

(21) Appl. No.: 18/360,394

(22) Filed: Jul. 27, 2023

(65) Prior Publication Data

US 2024/0032886 A1 Feb. 1, 2024

(30) Foreign Application Priority Data

Jul. 29, 2022 (TW) .................................. 111128659

(51) Int. Cl.
*A61B 7/00* (2006.01)
*A61B 5/00* (2006.01)
(Continued)

(52) U.S. Cl.
CPC ................ *A61B 7/003* (2013.01); *A61B 5/08* (2013.01); *A61B 5/113* (2013.01); *H04R 1/406* (2013.01);
(Continued)

(58) Field of Classification Search
CPC ......... A61B 5/003; A61B 5/008; A61B 5/113; A61B 5/6823; A61B 5/0816
See application file for complete search history.

(56) References Cited

U.S. PATENT DOCUMENTS

2006/0241510 A1* 10/2006 Halperin .............. A61B 5/7275
600/534
2020/0038708 A1* 2/2020 Cheu .................. A63B 71/0622

FOREIGN PATENT DOCUMENTS

EP       3701876 A1 * 9/2020 ............. A61B 7/003
JP    2003116818 * 4/2000
(Continued)

OTHER PUBLICATIONS

Kobayashi et al. (Year: 2014) English Translation of JP2014050614.*
Kozono et al. (Year: 2003) English Translation of JP2003116818.*

*Primary Examiner* — Brian T Gedeon
(74) *Attorney, Agent, or Firm* — Blank Rome LLP

(57) ABSTRACT

An equipment for monitoring physiological status of a user includes a sound detection unit, a chest detection unit, an abdomen detection unit, and a control unit. The sound detection unit is configured to detect sound of breath and to generate a sound detection signal based on the sound of breath. The chest detection unit is configured to detect a parameter related to movement of a chest and to generate a chest detection signal based on the detection. The abdomen detection unit is configured to detect a parameter related to movement of an abdomen and to generate an abdomen detection signal based on the detection. The control unit is electrically connected to the sound detection unit, the chest detection unit, and the abdomen detection unit and is configured to determine a breathing status of a user based on the sound detection signal, the chest detection signal, and the abdomen detection signal.

13 Claims, 2 Drawing Sheets

(51) Int. Cl.

| | | |
|---|---|---|
| *A61B 5/08* | (2006.01) | |
| *A61B 5/113* | (2006.01) | |
| *H04R 1/40* | (2006.01) | |
| *H04R 1/46* | (2006.01) | |
| *H04R 3/00* | (2006.01) | |
| *H04R 5/027* | (2006.01) | |
| *H04S 1/00* | (2006.01) | |

(52) U.S. Cl.

CPC .............. *H04R 1/46* (2013.01); *H04R 3/005* (2013.01); *H04R 5/027* (2013.01); *H04S 1/007* (2013.01); *A61B 5/6823* (2013.01); *A61B 2562/0204* (2013.01); *A61B 2562/0219* (2013.01); *A61B 2562/0261* (2013.01); *A61B 2562/06* (2013.01); *H04R 2410/01* (2013.01); *H04S 2400/15* (2013.01)

(56) References Cited

FOREIGN PATENT DOCUMENTS

| | | | | |
|---|---|---|---|---|
| JP | 2014050614 | * | 3/2014 | |
| WO | WO-2016166318 A1 | * | 10/2016 | .............. A61B 5/08 |
| WO | WO-2019241674 A1 | * | 12/2019 | ............. A61B 7/003 |

\* cited by examiner

EQUIPMENT FOR MONITORING PHYSIOLOGICAL STATUS

CROSS-REFERENCE TO RELATED APPLICATION

This application claims priority to Taiwanese Invention patent Application No. 111128659, filed on Jul. 29, 2022.

FIELD

The disclosure relates to an equipment for monitoring physiological status of a user, and more particularly to an equipment for monitoring breathing status of a user.

BACKGROUND

Upper airway resistance syndrome (UARS) is commonly found in elderly patients or occur due to degenerative reasons. The causes of UARS include retraction of the lower jaw, chronic nasal allergies, and teeth occlusal problems, which may increase upper airway resistance and lead to various clinical problems. Patients with mild UARS may experience sleep apnea as their primary manifestation; however, for elderly or unconscious patients, increased upper airway resistance may cause heavy breathing or even inhalation restriction due to the narrowed airway. This can result in reduced lung function, making it more difficult to cough up phlegm and worsening sleep apnea symptoms. The difficulty in clearing phlegm and the accumulation of phlegm in the throat may lead to the phlegm being inhaled into the trachea when the patient is in a lying position, potentially causing aspiration pneumonia and increasing hospitalization frequency, thus increasing burden on the caregivers. Furthermore, having narrowed airway or having phlegm in the airway may result in unsynchronized breathing between the chest and the abdomen during heavy breathing.

The prevalence of UARS is gradually increasing among the elderly population, and conventional medical care is unable to constantly and efficiently monitor the breathing conditions of patients with UARS.

SUMMARY

Therefore, an object of the disclosure is to provide an equipment for monitoring physiological status of a user that can alleviate at least one of the drawbacks of the prior art.

According to the disclosure, an equipment for monitoring physiological status of a user includes a sound detection unit, a chest detection unit, an abdomen detection unit, and a control unit. The sound detection unit is configured to detect sound attributed to breath of the user and to generate a sound detection signal based on the sound attributed to breath of the user. The chest detection unit is configured to detect a parameter related to movement of a chest of the user and to generate a chest detection signal based on the detection. The abdomen detection unit is configured to detect a parameter related to movement of an abdomen of the user and to generate an abdomen detection signal based on the detection. The control unit is electrically connected to the sound detection unit, the chest detection unit, and the abdomen detection unit. The control unit is configured to determine a breathing status of the user based on the sound detection signal, the chest detection signal, and the abdomen detection signal.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
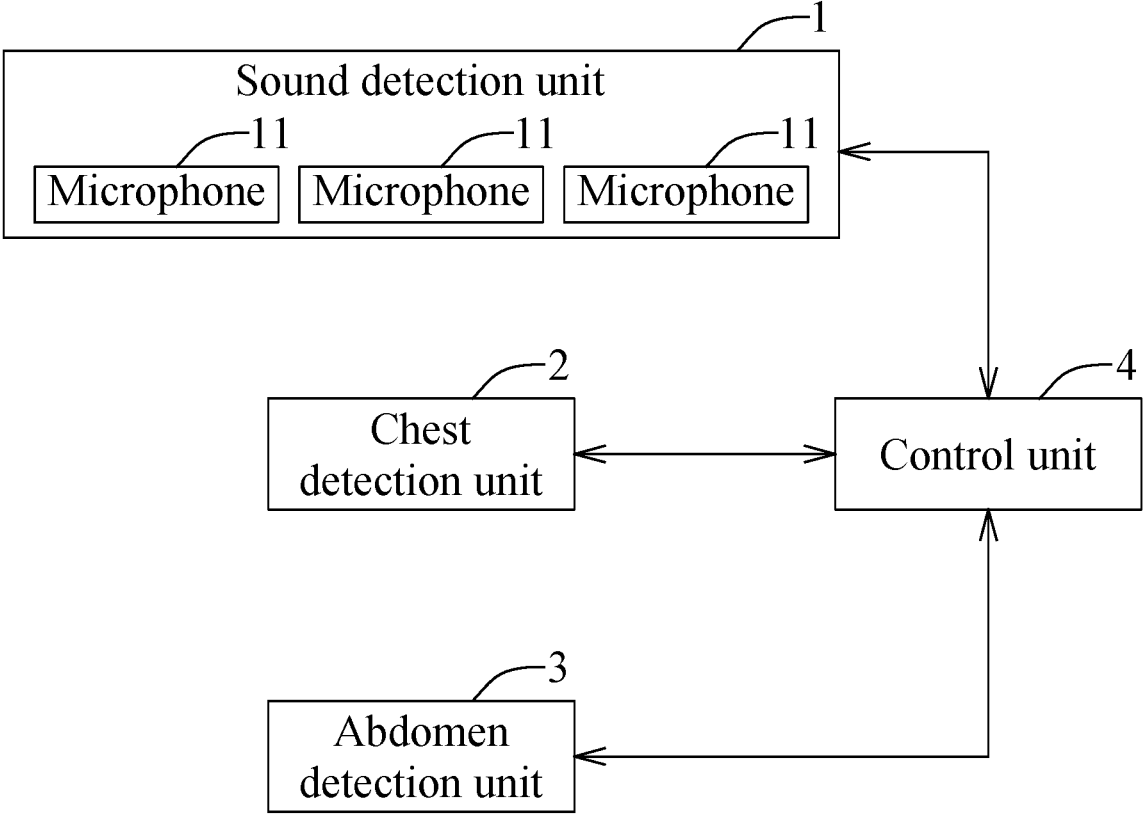
FIG. 1 is a block diagram illustrating an equipment for monitoring physiological status of a user according to an embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, an equipment for monitoring physiological status of a user according to an embodiment of the disclosure is provided. The equipment includes a sound detection unit 1, a chest detection unit 2, an abdomen detection unit 3, and a control unit 4 that is electrically connected to the sound detection unit 1, the chest detection unit 2, and the abdomen detection unit 3.

Figure 2:
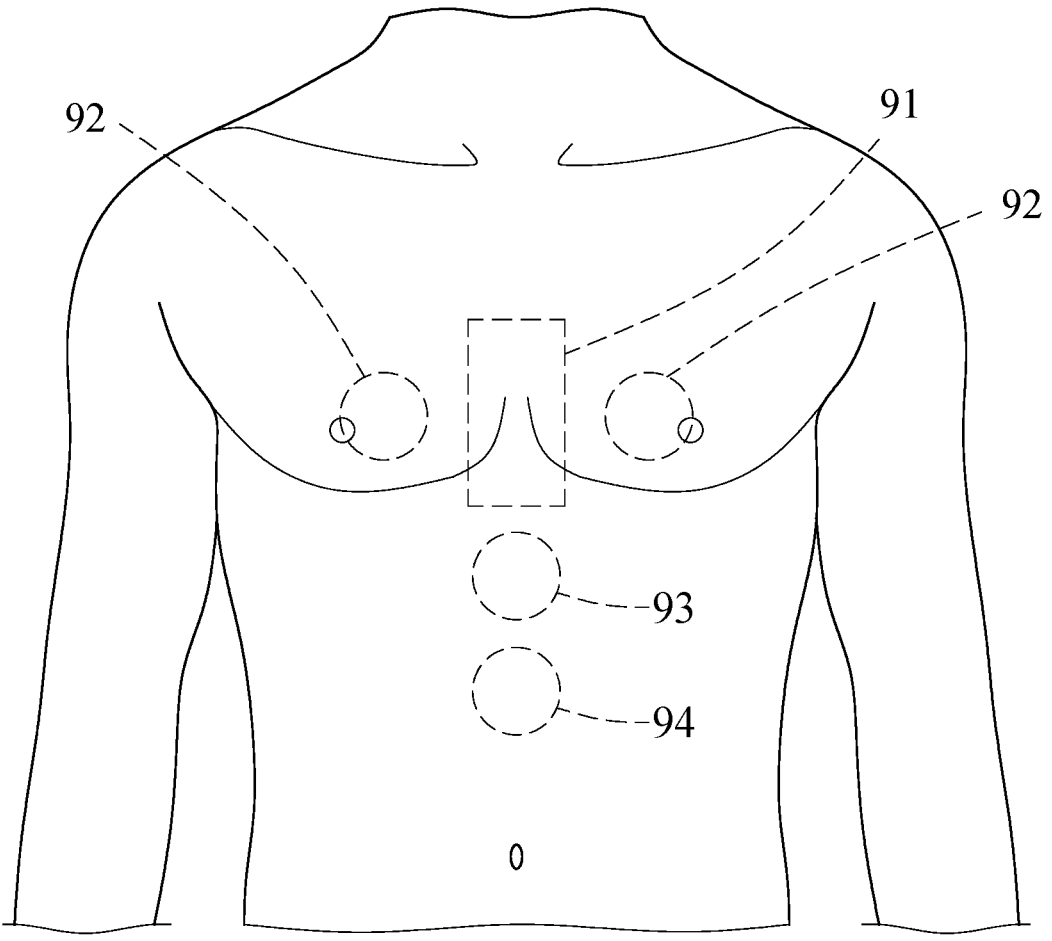
FIG. 2 is a schematic view illustrating positions of placement of components of the equipment on the user according to an embodiment of the disclosure.

The sound detection unit 1 is adapted to be disposed near the user, and is configured to detect sound attributed to breath of the user and to generate a sound detection signal based on the sound attributed to breath of the user. To describe in further detail, the sound detection unit 1 is adapted to be disposed near a left intercostal space that is to the left of the lower part of the sternum of the user and near a right intercostal space that is to the right of the lower part of the sternum of the user (i.e., at positions 92 shown in FIG. 2), which respectively correspond to a position of the left main bronchus and a position of the right main bronchus.

The sound detection unit 1 is configured to detect a left-chest sound from a left side of the chest and generate a left-chest sound detection signal based on the left-chest sound, and to detect a right-chest sound from a right side of the chest and generate a right-chest sound detection signal based on the right-chest sound, where the sound detection signal includes the left-chest sound detection signal and the right-chest sound detection signal.

In this embodiment, the sound detection unit 1 includes two microphones 11. In some embodiments, each of the two microphones 11 is a bone conduction microphone that is adapted to be attached to the skin of the user. The two microphones 11 are respectively attached to the skin near the left intercostal space and the skin near the right intercostal space (i.e., respectively at the positions 92 shown in FIG. 2), and are configured to respectively detect the left-chest sound and the right-chest sound to generate the left-chest sound detection signal and the right-chest sound detection signal. In some embodiments, each of the two microphones 11 of the sound detection unit 1 is a directional microphone. The two microphones 11 are adapted to be disposed to respectively point toward the left intercostal space and the right intercostal space, and are configured to respectively detect the left-chest sound and the right-chest sound to generate the left-chest sound detection signal and the right-chest sound detection signal.

The sound detection unit 1 may be further configured to detect ambient sound, and includes an additional microphone 11 that is adapted to be disposed near the user and to generate ambient sound detection signal based on the ambient sound. In such case, the sound detection signal further includes the ambient sound detection signal that is generated by the additional microphone. In some embodiments, the additional microphone is a microphone which may be attached to the skin near the neck of the user or attached to the skin near an ear of the user, and the ambient sound is detected by collecting sound signals that are within a predetermined frequency range. In some embodiments, the additional microphone 11 may be a microphone of a smartphone or an omnidirectional microphone, which may be disposed near the user for detecting the ambient sound close to the user in all directions.

The chest detection unit 2 is adapted to be disposed near the sternum of the user (at a position 91 shown in FIG. 2), and is configured to detect a parameter related to movement of the chest of the user and to generate a chest detection signal based on the detection. The chest detection unit 2 may include a three-axis accelerometer and a three-axis gyroscope that are cooperatively configured to detect the movement of the chest and to generate a chest acceleration signal based on the movement of the chest. The chest detection unit 2 may further include a first strain gauge that is adapted to be attached to the skin of the user at the chest and is configured to detect strain on the chest attributed to the movement of the chest and to generate a chest strain signal based on the strain on the chest. In this embodiment, the chest detection unit 2 includes the three-axis accelerometer, the three-axis gyroscope, and the first strain gauge, and the chest detection signal includes the chest acceleration signal and the chest strain signal. In some embodiments, the chest detection unit 2 may omit the first strain gauge, and the chest detection signal includes the chest acceleration signal. It should be noted that the quantity of the three-axis accelerometer, the quantity of the three-axis gyroscope, and the quantity of the first strain gauge in the chest detection unit 2 are not limited to one.

The abdomen detection unit 3 is adapted to be disposed near the abdomen of the user (for example, below the diaphragm, at position 94 shown in FIG. 2, or near the belly button of the user), and is configured to detect a parameter related to movement of the abdomen of the user and to generate an abdomen detection signal based on the detection. In this embodiment, the abdomen detection unit 3 includes a second strain gauge that is adapted to be attached to the skin of the user at the abdomen. The second strain gauge is configured to detect strain on the abdomen attributed to the movement of the abdomen and to generate an abdomen strain signal based on the strain on the abdomen. The abdomen detection signal includes the abdomen strain signal. In some embodiments, the abdomen detection unit 3 includes another three-axis accelerometer and another three-axis gyroscope that are cooperatively configured to detect the movement of the abdomen and to generate an abdomen acceleration signal based on the movement of the abdomen. It should be noted that the quantity of the three-axis accelerometer, the quantity of the three-axis gyroscope, and the quantity of the second strain gauge in the abdomen detection unit 3 is not limited to one.

In some embodiments, the equipment includes a sound detection unit 1, a chest detection unit 2, and a strain gauge. The chest detection unit 2 includes a three-axis accelerometer and a three-axis gyroscope that are cooperatively configured to detect the movement of the chest and to generate an acceleration signal based on the movement of the chest. The strain gauge is configured to generate a strain signal when the strain gauge is deformed due to the movement of the abdomen and the movement of the chest, and is adapted to be disposed between the sternum of the user and the abdomen of the user (for example, slightly closer to the abdomen than the chest, at position 93 shown in FIG. 2). In one example, if the movement of the chest and the movement of the abdomen are in opposite directions (i.e., one rising and one falling), the strain gauge would have significant deformation, and the strain gauge would generate the strain signal that indicates a large deformation, which suggests that the movement of chest and the movement of the abdomen are unsynchronized.

The control unit 4 may be, but is not limited to, a single core processor, a multi-core processor, a dual-core mobile processor, a microprocessor, a microcontroller, a digital signal processor (DSP), a field-programmable gate array (FPGA), an application specific integrated circuit (ASIC), a radio-frequency integrated circuit (RFIC), and/or a system on a chip (SoC), etc.

The control unit 4 is configured to, after receiving the sound detection signal from the sound detection unit 1, obtain breath sound of the user based on the left-chest sound detection signal and the right-chest sound detection signal. In the case where the sound detection signal further includes the ambient sound detection signal, the control unit 4 is configured to obtain the breath sound of the user by removing background noise from both the left-chest sound detection signal and the right-chest sound detection signal based on the ambient sound detection signal.

The control unit 4 is configured to, after receiving the chest acceleration signal, determine whether the chest of the user is rising or falling based on the chest acceleration signal. For example, in one embodiment, the equipment further includes a housing (not shown) with the three-axis accelerometer and the three-axis gyroscope being disposed therein, and a predetermined side of the housing is configured to be attached to the skin of the user. The control unit 4 may then determine rising or falling of the chest based on a sign change of the chest acceleration signal in a direction in which one of the three-axis accelerometer and the predetermined side of the housing is positioned relative to the other of the three-axis accelerometer and the predetermined side of the housing (i.e., based on variation of the acceleration indicated by the chest acceleration signal in the direction).

The control unit 4 is configured to, after receiving the chest strain signal from the chest detection unit 2 and the abdomen strain signal from the abdomen detection unit 3, determine whether the chest of the user is rising or falling based on the chest strain signal (e.g., a change in strain on the first strain gauge attributed to deformation or bending of the first strain gauge due to movement of the chest), and determine whether the abdomen of the user is rising or falling based on the abdomen strain signal (e.g., a change in strain on the second strain gauge attributed to deformation or bending of the second strain gauge due to movement of the abdomen).

The control unit 4 is further configured to determine a breathing status of the user based on the sound detection signal, the chest detection signal, and the abdomen detection signal. To describe in further detail, the control unit 4 is configured to determine that the user is inhaling while practicing abdominal breathing when the control unit 4 obtains the breath sound (i.e., the user is breathing) and determines both the chest and the abdomen being rising, to determine that the user is exhaling while practicing abdominal breathing when the control unit 4 obtains the breath sound and determines both the chest and the abdomen being falling, to determine that the user is inhaling while practicing chest breathing when the control unit 4 obtains the breath sound, determines the chest being rising, and determines the abdomen being falling, and to determine that the user is exhaling while practicing chest breathing when the control unit 4 obtains the breath sound, determines the chest being falling, and determines the abdomen being rising.

The control unit 4 is configured to obtain three sets of normal characteristics respectively for the sound detection signal, the chest detection signal, and the abdominal detection signal respectively based on the sound detection signal, the chest detection signal, and the abdomen detection signal that are generated when the user is breathing normally. That is to say, the sets of normal characteristics are obtained based on the sound detection signal, the chest detection signal, and the abdomen detection signal that are generated based on the sound attributed to normal breath of the user, normal movement of the chest of the user, and normal movement of the abdomen of the user. For example, the set of normal characteristics corresponding to the sound detection signal includes a range of frequency and a range of amplitude of the sound detection signal that is generated based on the sound attributed to normal breath of the user. In this embodiment, for the chest detection signal that includes the chest acceleration signal and the chest strain signal, the set of normal characteristics includes a range of frequency and a range of amplitude of the chest acceleration signal, and a range of frequency and a range of amplitude of the chest strain signal. As for the abdomen detection signal that includes the abdomen strain signal, the set of normal characteristics includes a range of frequency and a range of amplitude of the abdomen strain signal.

The control unit 4 stores a plurality of sound characteristics and a vibration characteristic, and the plurality of sound characteristics and the vibration characteristic may each include a range of frequency and a range of amplitude. For example, the plurality of sound characteristics may include three sound characteristics that respectively correspond to crackles, wheezing, and a sound attributed to phlegm, the vibration characteristic corresponds to vibration of phlegm, and the control unit 4 may be configured to compare the breath sound of the user with each of the three sound characteristics for determining whether the breath sound of the user has crackles, wheezing, or a sound attributed to phlegm, and to compare the chest acceleration signal with the vibration characteristic for determining whether the user has phlegm when the user is breathing.

The control unit 4 is configured to determine the breathing status of the user based on three factors, where a first factor relates to a relationship between the sound detection signal and the corresponding set of normal characteristics, a relationship between the chest detection signal and the corresponding set of normal characteristics, and a relationship between the abdomen detection signal and the corresponding set of normal characteristics; a second factor relates to the sound characteristics; and a third factor relates to the vibration characteristic.

In one example, the control unit 4 is configured to determine that the user is experiencing pneumonia when determining that the chest strain signal conforms with the set of normal characteristics for the chest detection signal and the abdomen strain signal conforms with the set of normal characteristics for the abdomen detection signal (i.e., the chest strain signal is within the range of frequency and the range of amplitude of the chest strain signal, and the abdomen strain signal is within the range of frequency and the range of amplitude of the abdomen strain signal) (namely, determining that the user is breathing normally), that the breath sound of the user has both crackles and wheezing or has a sound attributed to phlegm, and that the chest acceleration signal conforms with the vibration characteristic (i.e., the user has phlegm while breathing). In some embodiments, the control unit 4 omit the determination as to whether the user is breathing normally when making the determination as to whether the user is experiencing pneumonia. The control unit 4 may further determine an amount of phlegm based on the sound detection signal. For example, an increase in occurrence frequency of disruptions in the sound detection signal indicates that a high amount of phlegm exists. The control unit 4 may further determine whether the user is coughing based on the chest acceleration signal. For example, an abrupt change in amplitude of the chest acceleration signal may indicate that the user is coughing; the more abrupt the change, the more severe the coughing.

In another example, the control unit 4 is configured to determine that the user is experiencing a severe asthma attack when determining that the movement of the chest and the movement of the abdomen are unsynchronized (i.e., the movement of the chest and the movement of the abdomen are in opposite directions, meaning that one is rising and the other is falling) based on the chest strain signal and the abdomen strain signal, that the breath sound of the user when the user is exhaling has wheezing, and that the chest acceleration signal conforms with the set of normal characteristics that corresponds to the chest detection signal (i.e., the chest acceleration signal does not conform with vibration characteristic of phlegm).

The control unit 4 is further configured to calculate a first time difference between the user inhaling and the user exhaling based on the left-chest sound detection signal, and a second time difference between the user inhaling and the user exhaling based on the right-chest sound detection signal, and to determine whether the left lung of the user and the right lung of the user are breathing in synchronization based on the first time difference and the second time difference. To describe in further detail, the control unit 4 compares the first time difference and the second time difference, and determines that the left lung and the right lung are breathing in synchronization when the first time difference is substantially equal to the second time difference.

In summary, the equipment according to the disclosure is capable of, based on the sound detection signal, the chest detection signal, and the abdomen detection signal, determining the breathing status of the user, determining whether the breath sound of the user has crackles, wheezing, or a sound attributed to phlegm, determining whether the user is inhaling or exhaling, calculating a time difference between the user inhaling and the user exhaling, and obtaining the normal characteristics. A medical personnel may then provide proper care to the user (i.e., the patient) based on the determinations made by the equipment.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. An equipment for monitoring physiological status of a user, comprising:

a sound detection unit configured to detect sound attributed to breath of the user and to generate a sound detection signal based on the sound attributed to breath of the user;

a chest detection unit configured to detect a parameter related to movement of a chest of the user and to generate a chest detection signal based on the detection;

an abdomen detection unit configured to detect a parameter related to movement of an abdomen of the user and to generate an abdomen detection signal based on the detection; and a control unit electrically connected to said sound detection unit, said chest detection unit, and said abdomen detection unit, said control unit being configured to determine a breathing status of the user based on the sound detection signal, the chest detection signal, and the abdomen detection signal, wherein said sound detection unit is adapted to be disposed near a left intercostal space that is to a left of a lower part of a sternum of the user and near a right intercostal space that is to a right of the lower part of the sternum of the user, and is configured to detect a left-chest sound from a left side of the chest and generate a left-chest sound detection signal based on the left-chest sound, and detect a right-chest sound from a right side of the chest and generate a right-chest sound detection signal based on the right-chest sound, where the sound detection signal includes the left-chest sound detection signal and the right-chest sound detection signal, wherein said chest detection unit is adapted to be disposed near the sternum of the user, wherein said abdomen detection unit is adapted to be disposed near the abdomen of the user, wherein said sound detection unit includes two microphones that are adapted to be disposed respectively near the left intercostal space and the right intercostal space and that are configured to respectively generate the left-chest sound detection signal and the right-chest sound detection signal, wherein said chest detection unit includes a three-axis accelerometer and a three-axis gyroscope that are cooperatively configured to detect the movement of the chest and to generate an acceleration signal based on the movement of the chest, where the chest detection signal includes the acceleration signal, wherein said abdomen detection unit includes a strain gauge that is configured to detect strain on the abdomen attributed to the movement of the abdomen and to generate an abdomen strain signal based on the strain on the abdomen, where the abdomen detection signal includes the abdomen strain signal, wherein said chest detection unit further includes another strain gauge that is configured to detect strain on the chest attributed to the movement of the chest and to generate a chest strain signal based on the strain on the chest, where the chest detection signal further includes the chest strain signal, wherein said control unit is configured to obtain breath sound of the user based on the left-chest sound detection signal and the right-chest sound detection signal, to determine whether the chest of the user is rising or falling based on the chest detection signal, and to determine whether the abdomen of the user is rising or falling based on the abdomen detection signal, wherein said control unit is configured to obtain three sets of normal characteristics respectively for the sound detection signal, the chest detection signal, and the abdomen detection signal respectively based on the sound detection signal, the chest detection signal, and the abdomen detection signal that are generated when the user is breathing normally, and is configured to determine the breathing status of the user based on a relationship between the sound detection signal and the set of normal characteristics for the sound detection signal, a relationship between the chest detection signal and the set of normal characteristics for the chest detection signal, and a relationship between the abdomen detection signal and the set of normal characteristics for the abdomen detection signal, wherein one of the three sets of normal characteristics that corresponds to the sound detection signal includes a range of frequency and a range of amplitude of the sound detection signal, wherein one of the three sets of normal characteristics that corresponds to the chest detection signal includes a range of frequency and a range of amplitude of the acceleration signal, and a range of frequency and a range of amplitude of the chest strain signal, and wherein one of the three sets of normal characteristics that corresponds to the abdomen detection signal includes a range of frequency and a range of amplitude of the abdomen strain signal.

2. The equipment as claimed in claim 1, wherein each of said microphones of said sound detection unit is a bone conduction microphone adapted to be attached to skin of the user.

3. The equipment as claimed in claim 1, wherein each of said microphones of said sound detection unit is a directional microphone.

4. The equipment as claimed in claim 1, wherein said control unit stores a vibration characteristic that corresponds to vibration of phlegm, and said control unit is configured to compare the acceleration signal with the vibration characteristic for determining whether the user has phlegm when the user is breathing, and to determine an amount of phlegm based on the sound detection signal.

5. The equipment as claimed in claim 1, wherein said sound detection unit further includes another microphone that is adapted to be disposed near the user and that is configured to detect ambient sound and to generate an ambient sound detection signal based on the ambient sound, where the sound detection signal further includes the ambient sound detection signal.

6. The equipment as claimed in claim 5, wherein said control unit is configured to obtain breath sound of the user by removing background noise from both the left-chest sound detection signal and the right-chest sound detection signal based on the ambient sound detection signal.

7. The equipment as claimed in claim 1, wherein said control unit is further configured to determine that the user is inhaling while practicing abdominal breathing when the control unit obtains the breath sound and determines both the chest and the abdomen being rising, and to determine that the user is exhaling while practicing abdominal breathing when the control unit obtains the breath sound and determines both the chest and the abdomen being falling.

8. The equipment as claimed in claim 1, wherein said control unit is further configured to determine that the user is inhaling while practicing chest breathing when the control unit obtains the breath sound, determines the chest being rising, and determines the abdomen being falling, and to determine that the user is exhaling while practicing chest breathing when the control unit obtains the breath sound, determines the chest being falling, and determines the abdomen being rising.

9. The equipment as claimed in claim 1, wherein said control unit stores three sound characteristics that respectively correspond to crackles, wheezing, and a sound attributed to phlegm, and said control unit is configured to compare the breath sound of the user with each of the three sound characteristics for determining whether the breath sound of the user has crackles, wheezing, or a sound attributed to phlegm.

10. The equipment as claimed in claim 9, wherein:
said chest detection unit includes a three-axis accelerometer and a three-axis gyroscope that are cooperatively configured to detect the movement of the chest and to generate an acceleration signal based on the movement of the chest, where the chest detection signal includes the acceleration signal; and
said control unit further stores a vibration characteristic that corresponds to vibration of phlegm, and said control unit is configured to compare the acceleration signal with the vibration characteristic for determining whether the user has phlegm when the user is breathing, and to determine that the user is experiencing pneumonia when determining that the breath sound of the user has both crackles and wheezing or has a sound attributed to phlegm, and that the user has phlegm based on the comparison between the acceleration signal and the vibration characteristic.

11. The equipment as claimed in claim 9, wherein:
said abdomen detection unit includes a strain gauge that is configured to detect strain on the abdomen attributed to the movement of the abdomen and to generate an abdomen strain signal based on the strain on the abdomen, where the abdomen detection signal includes the abdomen strain signal;
said chest detection unit includes another strain gauge that is configured to detect strain on the chest attributed to the movement of the chest and to generate a chest strain signal based on the strain on the chest, where the chest detection signal further includes the chest strain signal; and
said control unit is configured to determine whether the movement of the chest and the movement of the abdomen are unsynchronized based on the chest strain signal and the abdomen strain signal, and to determine that the user is experiencing asthma when determining that the breath sound of the user when the user is exhaling has wheezing, that the chest detection signal conforms with the set of normal characteristics that corresponds to the chest detection signal when the user is breathing normally, and that the movement of the chest and the movement of the abdomen are unsynchronized based on the chest strain signal and the abdomen strain signal.

12. The equipment as claimed in claim 1, wherein said control unit is configured to calculate, for each of the left-chest sound detection signal and the right-chest sound detection signal, a time difference between the user inhaling and the user exhaling, and determine whether a left lung of the user and a right lung of the user are breathing in synchronization based on the time differences respectively of the left-chest sound detection signal and the right-chest sound detection signal.

13. The equipment as claimed in claim 1, wherein:
said sound detection unit includes two microphones that are adapted to be disposed respectively near the left intercostal space and the right intercostal space and that are configured to respectively generate the left-chest sound detection signal and the right-chest sound detection signal;
said chest detection unit includes a three-axis accelerometer and a three-axis gyroscope that are cooperatively configured to detect the movement of the chest and to generate an acceleration signal based on the movement of the chest, where the chest detection signal includes the acceleration signal; and
said abdomen detection unit includes another three-axis accelerometer and another three-axis gyroscope that are cooperatively configured to detect the movement of the abdomen and to generate another acceleration signal based on the movement of the abdomen, where the abdomen detection signal includes the another acceleration signal.

* * * * *